(12) United States Patent
Legge

(10) Patent No.: US 8,370,170 B2
(45) Date of Patent: Feb. 5, 2013

(54) SYSTEM FOR CONTROLLING A PHYSICAL TASK

(76) Inventor: Jenny Legge, Mount Pleasant (AU)

( * ) Notice: Subject to any disclaimer, the term of this patent is extended or adjusted under 35 U.S.C. 154(b) by 1462 days.

(21) Appl. No.: 10/497,366

(22) PCT Filed: Dec. 2, 2002

(86) PCT No.: PCT/AU02/01627
§ 371 (c)(1),
(2), (4) Date: Nov. 18, 2004

(87) PCT Pub. No.: WO03/047431
PCT Pub. Date: Jun. 12, 2003

(65) Prior Publication Data
US 2005/0108087 A1  May 19, 2005

(30) Foreign Application Priority Data
Dec. 3, 2001  (AU) .................................. PR9257

(51) Int. Cl.
*G06Q 10/00* (2012.01)
(52) U.S. Cl. ............ 705/2; 600/300; 600/483; 600/513; 434/407; 434/117
(58) Field of Classification Search .................. 600/300; 707/104.1; 705/38
See application file for complete search history.

(56) References Cited

U.S. PATENT DOCUMENTS

| | | | |
|---|---|---|---|
| 4,520,060 A | 5/1985 | Blumle | |
| 5,176,521 A | 1/1993 | McRae | |
| 5,616,032 A | 4/1997 | Keitzer et al. | |
| 5,706,822 A | 1/1998 | Khavari | |
| 5,778,882 A | 7/1998 | Raymond et al. | |
| 6,050,924 A | 4/2000 | Shea | |
| 6,440,067 B1 * | 8/2002 | DeLuca et al. | 600/300 |
| 6,865,581 B1 * | 3/2005 | Cloninger et al. | 707/104.1 |
| 7,006,992 B1 * | 2/2006 | Packwood | 705/38 |

FOREIGN PATENT DOCUMENTS

| | | |
|---|---|---|
| CA | 2175288 | 10/1997 |
| DE | 3830944 | 3/1990 |
| DE | 299 22 787 | 8/2000 |
| DE | 299 22 787 | 8/2010 |
| EP | 0821517 | 1/1998 |

(Continued)

OTHER PUBLICATIONS

European Examination Report for European Application No. 02 779 040.1, Dec. 16, 2009.

*Primary Examiner* — Valerie Lubin
(74) *Attorney, Agent, or Firm* — Austin Rapp & Hardman

(57) ABSTRACT

A system for controlling physical activity for a person, including the steps of providing a task database having a plurality of task files which each have data relating to physical task requirements for a person and a plurality of frequency requirements which indicate a frequency for performing a physical task for the particular type of task of the task file, providing a personal data file for a person including data relating to allowable physical tasks and allowable frequency limits for the person when performing the physical task, comparing one personal data file having a selected persons allowable physical task and allowable frequency limits data with a task file having data relating to physical task requirements and frequency requirements of the task type of the task file and from the comparison outputting an indication of whether the selected person is able to safely perform one or more physical tasks in the task file.

25 Claims, 9 Drawing Sheets

| Select a Division then Select a Job then Select a Worker | Division | Underground Coal |
|---|---|---|
| | Job | Development Fitter |
| | Worker | Tester, Terry |

| Task Title | Frequency | Work Postures Count | | Material Handling Count | |
|---|---|---|---|---|---|
| | | Suitable | Unsuitable | Suitable | Unsuitable |
| Hoses/cables, changing (excl shearer, cont | Regular | 35 | 4 | 8 | 4 |
| Hoses/cables, hanging | Regular | 30 | 9 | 9 | 3 |
| LHD, driving | Regular | 34 | 5 | 12 | 0 |
| LHD, servicing | Regular | 31 | 8 | 12 | 0 |
| Mechanical Maintenance Services | Regular | 32 | 7 | 10 | 2 |
| PJB/Driftrunner, operation | Regular | 38 | 1 | 12 | 0 |
| PJB/Driftrunner servicing | Regular | 35 | 4 | 12 | 0 |
| Belt structure, erecting and dismantling | Irregular | 31 | 8 | 7 | 5 |
| Shovelling | Irregular | 32 | 7 | 12 | 0 |
| Shuttle Car, driving | Irregular | 29 | 0 | 12 | 0 |
| Ventilation Tubes, handing and retrieving | Irregular | 32 | 7 | 8 | 4 |
| Water pipes, hanging | Irregular | 31 | 8 | 8 | 4 |

FOREIGN PATENT DOCUMENTS

| | | |
|---|---|---|
| EP | 1151764 A2 | 11/2001 |
| EP | 1240865 | 9/2002 |
| WO | WO 94/10634 | 5/1994 |
| WO | WO 01/16855 A2 | 3/2001 |

* cited by examiner

| PHYSICAL TASK ANALYSIS SCORECARD ||||||||||||
|---|---|---|---|---|---|---|---|---|---|---|---|
| TASK TITLE |||||||||||||
| WORKING POSTURES |||||| MATERIAL HANDLING ||||||
| | R | O | F | C | N | | R | O | F | C | N |
| Back | | | | | | Bench | | | | | |
| Bend forward | | | | | | <1kg | | | | | |
| Bend backward | | | | | | 1-3 | | | | | |
| Rotate Left | | | | | | 3-5 | | | | | |
| Rotate Right | | | | | | 5-7 | | | | | |
| Combined | | | | | | 7-10 | | | | | |
| Neck | | | | | | 10-15 | | | | | |
| Look down | | | | | | 15-20 | | | | | |
| Look up | | | | | | 20-25 | | | | | |
| Rotate Left | | | | | | 25-30 | | | | | |
| Rotate Right | | | | | | 30-35 | | | | | |
| Combined | | | | | | >35 | | | | | |
| Shoulders | | | | | | Shoulder | | | | | |
| Reach overhead | | | | | | <1kg | | | | | |
| Reach Left | | | | | | 1-3 | | | | | |
| Reach Right | | | | | | 3-5 | | | | | |
| Reach behind | | | | | | 5-7 | | | | | |
| Reach forward | | | | | | 7-10 | | | | | |
| Wrist/Hand | | | | | | 10-15 | | | | | |
| Bent up | | | | | | 15-20 | | | | | |
| Bent down | | | | | | 20-25 | | | | | |
| Angle to thumb | | | | | | 25-30 | | | | | |
| Angle to 5th | | | | | | 30-35 | | | | | |
| Palm-down hold | | | | | | >35 | | | | | |
| Hands/Fingers | | | | | | Overhead | | | | | |
| Pinch grip | | | | | | <1kg | | | | | |
| Wide span | | | | | | 1-3 | | | | | |
| Manipulate | | | | | | 3-5 | | | | | |
| Vibration | | | | | | 5-7 | | | | | |
| Legs/Feet | | | | | | 7-10 | | | | | |
| Squat | | | | | | 10-15 | | | | | |
| Kneel | | | | | | 15-20 | | | | | |
| Foot pedals | | | | | | 20-25 | | | | | |
| Jump | | | | | | 25-30 | | | | | |
| General | | | | | | 30-35 | | | | | |
| Stand | | | | | | >35 | | | | | |
| Sit – supported | | | | | | Carry | | | | | |
| Sit – unsupported | | | | | | <1kg | | | | | |
| Walk indoors | | | | | | 1-3 | | | | | |
| Walk outdoors | | | | | | 3-5 | | | | | |
| Balancing | | | | | | 5-7 | | | | | |
| Climbing | | | | | | 7-10 | | | | | |
| Running | | | | | | 10-15 | | | | | |
| Crawling | | | | | | 15-20 | | | | | |
| Stooping | | | | | | 20-25 | | | | | |
| | | | | | | 30-35 | | | | | |
| | | | | | | >35 | | | | | |

Legend: C = Continuous  F = Frequent  O = Occasional  R = Rarely  N = Never  * = Comments apply Authorised Assessor        Signature        Date

FIG.1

| Last Name | Tester | | | | First Name | Terry | | | | Initials | TT | | | | Date of Birth | 28/9/1971 | | | |
|---|---|---|---|---|---|---|---|---|---|---|---|---|---|---|---|---|---|---|---|
| Back | N | O | F | C | Shoulders | N | O | F | C | Hand/Fingers | N | O | F | C | General | N | O | F | C |
| Bend Forward | | ⊙ | | | Reach Overhead | | ⊙ | | O | Pinch Grip | | | | C | Stand | | ⊙ | | C |
| Bend Backward | | | ⊙ | | Reach Left | | | | C | Wide Grip | | ⊙ | | C | Sit Supported | | ⊙ | | C |
| Rotate Left | | ⊙ | | | Reach Ridge | | | ⊙ | O | Manipulate | | | ⊙ | C | Sit Unsupported | | ⊙ | | C |
| Rotate Right | | | | ⊙ | Reach Behind | | | | O | Vibration | | | ⊙ | C | Walk Even | | ⊙ | | C |
| Combined | ⊙ | | | | Reach Forward | | | | N | Sustained Grip | | ⊙ | | C | Walk Uneven | | ⊙ | | O |
| Neck | N | O | F | C | Wrist/Hand | N | O | F | C | Legs/Feet | N | O | F | C | Balancing | | ⊙ | | C |
| Look Down | | ⊙ | | | Bent Up | | ⊙ | | C | Squat | | ⊙ | | C | Climbing | ⊙ | | | O |
| Look Up | | ⊙ | | | Bent Down | | ⊙ | | C | Kneel | | | ⊙ | C | Running | | ⊙ | | C |
| Rotate Left | | | ⊙ | | Angle to Thumb | | | ⊙ | C | Foot Pedals | | | ⊙ | C | Crawling | | ⊙ | | C |
| Rotate Right | | | ⊙ | | Angle to 5th | | ⊙ | | C | Jump | ⊙ | | | C | Stooping | ⊙ | | | N |
| Combined | | | | ⊙ | Palm-down Hold | | | ⊙ | C | | | | | | Vibration | ⊙ | | | O |

Legend: N = Never   O = Occasional   F = Frequent   C = Continuous

FIG.2

| Last Name | Tester | First Name | Terry | Initials | TT | Date of Birth | 28/09/1971 |

| | Occasional | Frequent | Continuous |
|---|---|---|---|
| Bench | 15 | 11 | 8.5 |
| Shoulder | 15 | 11 | 8.5 |
| Overhead | 15 | 11 | 8.5 |
| Carry | 15 | 11 | 8.5 |

| Select a Division then | Division | Underground Coal |
|---|---|---|
| Select a Job then | Job | Development Fitter |
| Select a Worker | Worker | Tester, Terry |

☐ All Jobs

| Task Title | Frequency | Work Postures Count | | Material Handling Count | |
|---|---|---|---|---|---|
| | | Suitable | Unsuitable | Suitable | Unsuitable |
| Hoses/cables, changing (excl shearer, cont | Regular | 35 | 4 | 8 | 4 |
| Hoses/cables, hanging | Regular | 30 | 9 | 9 | 3 |
| LHD, driving | Regular | 34 | 5 | 12 | 0 |
| LHD, servicing | Regular | 31 | 8 | 12 | 0 |
| Mechanical Maintenance Services | Regular | 32 | 7 | 10 | 2 |
| PJB/Driftrunner, operation | Regular | 38 | 1 | 12 | 0 |
| PJB/Driftrunner servicing | Regular | 35 | 4 | 12 | 0 |
| Belt structure, erecting and dismantling | Irregular | 31 | 8 | 7 | 5 |
| Shovelling | Irregular | 32 | 7 | 12 | 0 |
| Shuttle Car, driving | Irregular | 29 | 0 | 12 | 0 |
| Ventilation Tubes, handing and retrieving | Irregular | 32 | 7 | 8 | 4 |
| Water pipes, hanging | Irregular | 31 | 8 | 8 | 4 |

| Division | Underground Coal |
|---|---|
| Job | Development Fitter |
| Worker | Tester, Terry |

Select a Division then
Select a Job then
Select a Worker

☐ All Jobs

| | Occasional (Kgs) | | | Frequent (Kgs) | | | Continuous (Kgs) | | |
|---|---|---|---|---|---|---|---|---|---|
| | PTA | SWA | Fit | PTA | SWA | Fit | PTA | SWA | Fit |
| Bench | 35 | 15 | ☐ | 34 | 11 | ☐ | 3 | 8.5 | ☑ |
| Shoulder | 35 | 15 | ☐ | 34 | 11 | ☐ | | 8.5 | ☐ |
| Overhead | 35 | 15 | ☐ | 12 | 11 | ☐ | | 8.5 | ☐ |
| Carry | 35 | 15 | ☐ | 34 | 11 | ☐ | 3 | 8.5 | ☑ |

Awkward Handling ☐

FIG. 8.

SYSTEM FOR CONTROLLING A PHYSICAL TASK

BACKGROUND OF THE INVENTION

The present invention relates to health issues associated with individuals and is particularly concerned with occupational rehabilitation and injury prevention.

FIELD OF THE INVENTION

In a workplace environment tasks need to be carried out with minimal risk to the safety of the worker. Accordingly a worker with health disabilities may be unsuitable for particular tasks. Clearly it is in the best interests of an employer and worker to avoid having workers risk injury by performing tasks for which they are not suited.

Another issued to be considered is rehabilitation of workers or individuals who have experienced a health problem and must avoid performing tasks which are likely to endanger their health further or restrict recovery.

SUMMARY OF THE INVENTION

According to the present invention there is provided a system for controlling a physical task to be performed by a person, including a base means having a plurality of task options which are available to be performed by a person and a plurality of frequency options which each indicate a different frequency with which tasks can be performed, a template means for a person, having zones for indicators representing task options able to be performed by a person and the frequency option which is allocated to each task option for that person, whereby in use the template means is adapted to be provided with indicators representing physical abilities of a person and then placed over a base means having indicia representing physical requirements for a task, whereby if the persons indicators overlap the indicia, the person is assessed as being physically capable of performing the tasks indicated by the medium.

It is preferred that the base means comprises a base member.

According to an alternative application the base means is in the form of a pictorial representation on a computer screen or the like.

The template means may be a template member or device which is adapted to overlay the base member.

According to a computer application the template means may be pictorially represented on a computer screen or the like.

According to the computer application of the invention separate data bases are established for the different tasks of the base means as well as the different frequency options of the base means.

In the computer application the template means may also be a database having task options and frequency options for individuals.

Preferably the base member has a plurality of rows and columns.

The base member preferably comprises a supporting medium with the rows and columns forming boxes adapted to receive indicia.

Preferably each row includes a particular task which is available to be performed by any person.

Preferably each column includes a particular frequency with which tasks can be performed.

A particular task may include bending the person's back forward or backwards or moving the person's neck forwards or backwards or sideways.

The template means preferably comprises a template member.

The template is preferably substantially transparent.

The indicators may comprise markings which are to be placed at locations corresponding to the boxes of the base member.

The template may be substantially the same as the base member except that the supporting medium is transparent.

The template may include rows and columns forming boxes, which are to be marked with indicators for task options and frequency options allocated based on the physical abilities of a particular person.

It is preferred that a single template includes indicators for task options and frequency options for one person.

Preferably in the computer application the system includes a processing means for pictorially representing the template means overlaying the base means.

The processing means may be adapted to compare the location of indicators of the template means with the location of the indicia of the base means and output an approval or disapproval representation if the indicators overlap the indicia or do not.

It is preferred that a plurality of base means are provided each being provided with indicia representing task options and frequency options required for a particular task.

Preferably the base means and the template means each have alignment means to enable the template means to be aligned properly with the base means so that task options and frequency options are properly aligned so that the indicator of a task option and frequency option of the template means covers the indicia of the same task option and frequency option of the base means.

According to another aspect of the present invention there is provided a system for controlling physical activity for a person, including the steps of providing a task data base having a plurality of task files which each have data relating to physical task requirements for a person and a plurality of frequency requirements which indicate a frequency for performing a physical task for the particular type of task of the task file, providing a personal data file for a person including data relating to allowable physical tasks and allowable frequency limits for the person when performing the physical task, comparing one personal data file having a selected persons allowable physical task and allowable frequency limits data with a task file having data relating to physical task requirements and frequency requirements of the task type of the task file and from the comparison outputting an indication of whether the selected person is able to safely perform one or more physical tasks in the task file.

It is preferred that the comparing step is performed by a comparison means.

Preferably the comparison means comprises a plurality of comparison procedures including comparing each physical task requirement with each allowable physical task.

The comparison means preferably compares each allowable frequency limit data for each physical task with the frequency requirement data of each physical task required for the task type in the task file.

Preferably the system includes the step of storing a plurality of personal data files.

Each personal data file preferably comprises a worker file having data relating to an employee.

It is preferred that the person includes a patient, worker, athlete or any other person including an animal which needs to have controlled physical activity, particularly as a result of a disability, permanent or temporary.

It is preferred that the system includes providing a patient database having a plurality of patient files.

It is preferred that each task file includes a plurality of physical tasks and a plurality of frequency options.

Each task file may include a physical task analysis for the task including a plurality of different physical tasks and an indication of the frequency options for performing each physical task.

The indication of the frequency option may include never, rarely, occasionally, frequently and continuously.

The physical task analysis may be displayed in a table format with physical tasks arranged in rows and frequency options in columns.

Each physical task may have the same possible frequency option.

It is preferred that the physical tasks include tasks performed by different parts of the body/muscles etc.

Preferably the physical tasks include different working postures, which are sometimes referred to herein as "work postures."

The different working postures may include any of those described in the preferred embodiment of the invention.

Preferably the physical tasks include material handling requirements.

Each task file may include physical task/frequency options displayed with markings indicating frequency with which each physical task is required for the task type of that file.

Each physical task may include physical weight handling analysis.

It is preferred that each physical task includes an indication of required physical weight to be handled by a person performing the task.

It is preferred that each physical task includes an indication of the frequency of handling the weight.

Each physical weight handling analysis preferably includes a display of different weight handling options against the frequency required for performing the weight handling option.

Each physical weight handling analysis preferably includes a display of the type of handling required for the different weight handling options.

Preferably different weight handling options include different ranges of weights such as 1 kilogram, 1 to 3 kilograms, 3 to 5 kilograms etc.

It is preferred that different weight handling types include bench, shoulder, overhead, carrying, pushing, pulling etc.

The task file may include a summary display page.

Preferably the physical task analysis is displayed on a physical task versus frequency electronic page.

The physical task versus frequency page includes a display of working posture versus frequency option and/or material handling versus frequency option.

It is preferred that separate display pages are provided for each of the above.

Preferably a patient file includes a physical task analysis including a display of each physical task versus frequency options for that task and an indication of any physical task which can be performed safely.

Preferably the physical tasks include safe working posture and material handling.

The system may include a materials handling calculator for calculating a materials handling value for each material handling option performed at a particular frequency.

The material handling calculator preferably includes a safe material handling value for representing a safe value of material handling able to be safely performed by a patient.

The comparison means preferably includes a comparison display.

The comparison display may include a list of tasks and a suitability indicator which indicates whether a patient is suitable for each task.

The comparison means may include means for entering the name of a patient and entering the name of a task.

It is preferred that the comparison means displays suitable and unsuitable physical tasks for each task type.

Preferably the comparison display includes a working postures count value for each task type, the count value being indicative of usage of the working posture.

The comparison display may include a materials handling count value for each task type which count value is indicative of the degree of usage of the material handling option.

It is preferred that the comparison display includes a table of task type versus working posture and/or material handling and suitability or unsuitability for performing each of the work postures and each of the material handling options for each task type.

Preferably the comparison display includes a working postures fit display such as a table.

The working postures fit display may include a list of working postures and a physical task analysis for the task type and safe working ability for the patient for the task.

The working postures display preferably includes a fit indicator for each working posture which is suitable for the patient.

The comparison means may be adapted to provide a fit indicator whenever these safe working ability is greater than the physical task requirement for a particular physical task.

Preferably the comparison display includes a material handling display including a table having different material handling options/types and a physical task analysis and a safe working ability analysis for each frequency option.

It is preferred that each physical task requirement is represented by the material handling value for each material handling option performed at a particular frequency.

The safe working ability is represented by the safe material handling value.

According to another aspect of the present invention there is provided a computer program for controlling physical activity for a person including operations to provide a task database having a plurality of task files which each have data relating to physical task requirements for a person and a plurality of frequency requirements which indicate a frequency for performing a physical task for a particular type of task, providing a personal data file for a person including data relating to allowable physical tasks and allowable frequency limits for the person when performing a task, a comparison means for comparing a file having a selected persons allowable physical tasks and allowable frequency limits data with a task file having data relating to physical task requirements and frequency requirements of a task and outputting from the comparison means an indication of whether the person is able to safely perform the task from the compared data from the comparison means.

It is preferred that the computer program also includes one or more of the preferred options of the system previously defined.

The comparison display may include a fit indicator for indicating when the safe working ability is greater than the physical task requirement (PTA).

The words "comprising, having, including" should be interpreted in an inclusive sense, meaning that additional features may also be added.

BRIEF DESCRIPTION OF THE DRAWINGS

FIG. 1 shows different task options and frequency options according to an embodiment of the invention implemented using a physical support medium;

FIG. 2 shows a display page of a patient file with a safe working ability table;

FIG. 3 shows a display page of the patient file having a table of safe working ability for material handling options;

FIG. 4 shows a display of a task file page having a table of working postures for physical tasks;

FIG. 6 shows a display of a comparison table showing suitable/unsuitable work postures or material handling for a particular task;

FIG. 7 shows a comparison table of working postures fits for a patient;

FIG. 8 shows a comparison table of material handling fits for a patient; and

DETAILED DESCRIPTION OF THE DRAWINGS

Figure 5:
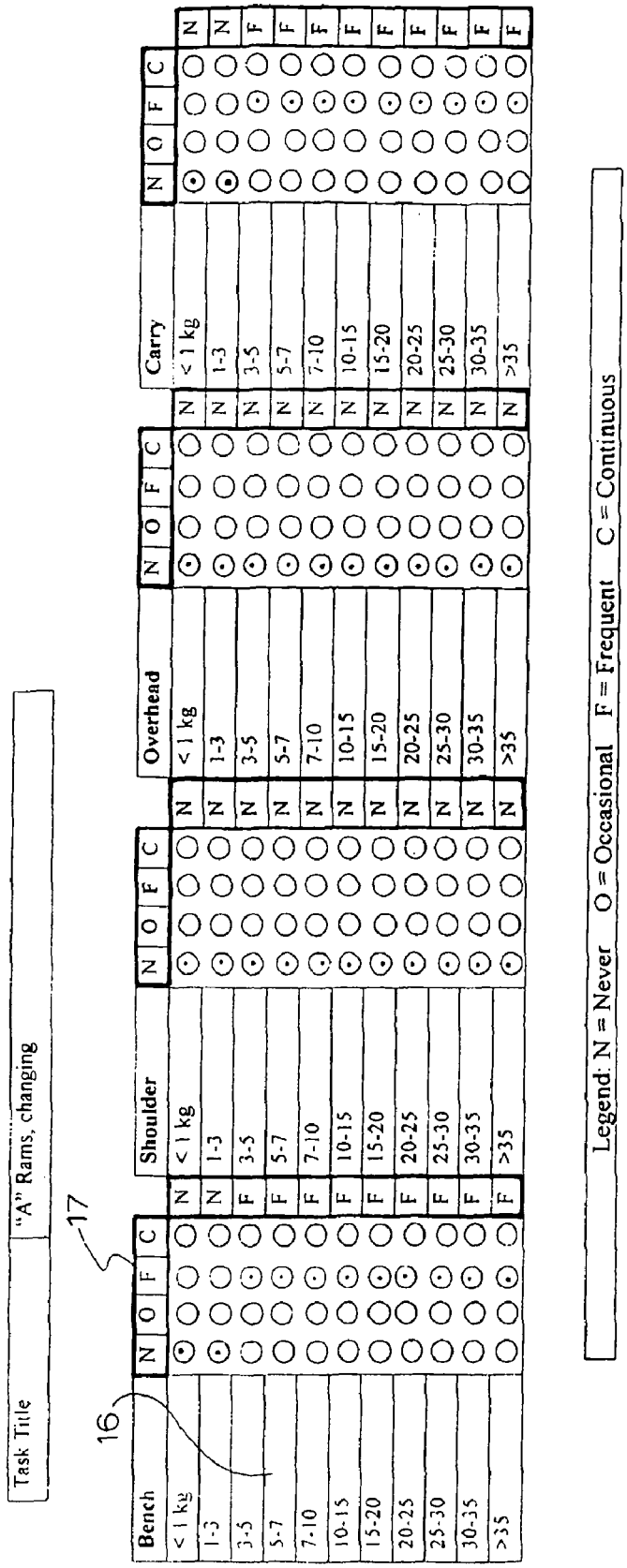
FIG. 5 shows a display of a page of a task file having a table showing material handling versus frequency requirements.

A preferred embodiment of the present invention will now be described by way of example only with reference to FIG. 1 which shows a physical task option sheet in accordance with the preferred embodiment of the invention.

According to the preferred embodiment of the invention an individual is physically assessed by a suitably qualified healthcare professional to determine that individual's suitability for a particular workplace task.

To begin with, workplace rehabilitation coordinators and other occupational health and safety personnel are registered as authorised system assessors for controlling physical tasks.

Next a physical task analysis of all required tasks is established in the form of the physical task option sheet shown in FIG. 1.

The possible tasks as provided in different columns in FIG. 1 include working postures, such as those associated with the back, neck, shoulders, elbow, forearm, wrist/hand, hand/fingers, leg/feet and general tasks such as walking.

Furthermore the different weightlifting options available for an individual are also listed in separate columns in a second half of the physical task options sheet. These lifting options include lifting a particular weight from the floor, from a bench, from the shoulders, or overhead and carry.

As each individual has a different capability for the above tasks, different frequency options are given and these include sustained, continuous, frequently, occasionally, rarely and never.

The frequency options may be changed so as to be specific for time periods. Likewise the physical tasks may be changed to isolate particular muscle groups.

As shown in FIG. 1 the different task options and frequency options are presented on the sheet (support medium) as a series of boxes which are able to be marked.

At the top of each column the letter R represents rarely, O occasionally, F frequently, C continuously and N never.

Each row is headed by a particular action such as bending forward or bending backward. In addition the particular actions are grouped according to which part of the body they relate to. Thus groupings include those relating to the back, neck, shoulders, wrists/hand, hands, fingers, legs/feet, bench, shoulder, overhead, carry, general.

For each physical task that may be performed in for example a workplace, a separate physical task option sheet is prepared, by marking a tick in the appropriate boxes. If a physical demand lies within a range of the material handling requirements, it is preferred to always go to the higher value.

Each rehabilitation coordinator will have a file containing physical task option sheets for each task description.

If an injured worker wishes to apply for a workplace task, the injured worker must firstly consult with their treating medical officer and rehabilitation coordinator to obtain documented evidence of the workers safe working capacity. A safe working capacity (ability) template is created having the same layout as the physical task options sheet. Thus the workers safe working capacity for particular task options as well as the frequency suitable for carrying out those task options are marked in the boxes provided in the transparent safe working capacity sheet.

Once the template has been created the rehabilitation coordinator retrieves a physical task options sheet from the relevant file for the particular task to which the individual intends to perform.

The template is then placed over the base physical task option sheet (scorecard) and if the workers abilities as indicated by ticks in boxes overlap the marked physical requirements of the task, then the individual is considered suitable for that task. If the opposite occurs and some of the marked boxes of the template do not overlap the marked boxes of the base sheet, then the individual is considered not to be suitable for that task outlined on the base sheet.

By using the above system an individual can visit an approved rehabilitation coordinator and the coordinator can identify a task for which that individual is suitable.

The above procedures can also be used for people who have existing medical conditions which limit the physical tasks they are able to perform and also in the pre-employment process.

The way in which the different frequencies are classified may also change as set out below.

TABLE 1

| Classification of Frequencies | | | | |
|---|---|---|---|---|
| | % of Workday | Reps per Day | Reps per Hour | Reps per Minute |
| Continuous | 67-100 | 500+ | >63 | 1 or more |
| Frequent | 34-66 | 101-500 | 12-63 | 1 every 1-5 |
| Occasional | 1-33 | 1-200 | 0-2 | 1 every 5 |
| Never | Not required | | | |

Source: Dictionary of Occupational Titles, US Dept of Labour.

Thus a continuous frequency may entail 67 to 100% of a work day, include 500 repetitions per day, greater than 62 repetitions per hour and one or more repetitions per minute.

A guide may also be provided for calculating safe material handling tolerances as set out in Table 2 below.

TABLE 2

Guide of Calculating Safe Material Handling Tolerances

| Maximal Safe Lifting Restriction | | Frequency Factor | | Awkward Load Percentage* | | Safe Material Handling Tolerance |
|---|---|---|---|---|---|---|
| Continuous | X | 0.57 | X | 0.75 | = | |
| Frequent | X | 0.75 | X | 0.75 | = | |
| Occasional | X | 1.00 | X | 0.75 | = | |

*It is recommended that the "Awkward Load Percentage" be applied to loads that are difficult to handle, inaccessible or awkward.
Source: "WorkHab Australia" Functional Capacity Profiling Procedure Manual.

A set procedure is established for linking the functions of the medical officer assessing the capabilities of a person with the tasks required of that person if employed to do a particular job. If the medical officer is a suitably qualified healthcare professional then they can test the capabilities of the individual, complete a template, being a safe working ability score card and compare this with the pre-established base physical task option sheet which includes an itemised account of the particular tasks and the frequency of those tasks which are required to perform the job.

The authorised medical officer can then advise the individual of their suitability for the job they have applied for.

In addition the medical officer is able to compare the individuals safe working ability template, which indicates their capabilities with different base physical task analysis score cards to identify those tasks for which the individual has the required abilities.

Although the preferred embodiment of the invention has been described in relation to information stored on physical media such as sheets of paper, the invention can also be implemented in a computer program. In such an implementation a base physical task option score card is provided for each task or job and stored in a data base. An individual is then assessed by a suitably qualified healthcare professional who if authorised as a rehabilitation coordinator is able to prepare a safe working ability score card and store this in a file on a computer. The computer can then be programmed to compare the task and frequency option abilities of the individual with the task scorecards scored in the base physical task option scorecard data base. If the safe working ability scorecard has task options and frequency options which correspond with those of any one or more of the physical task analysis scorecards then the jobs represented by those physical task analysis scorecards are available to be performed by the individual.

Figure 4:
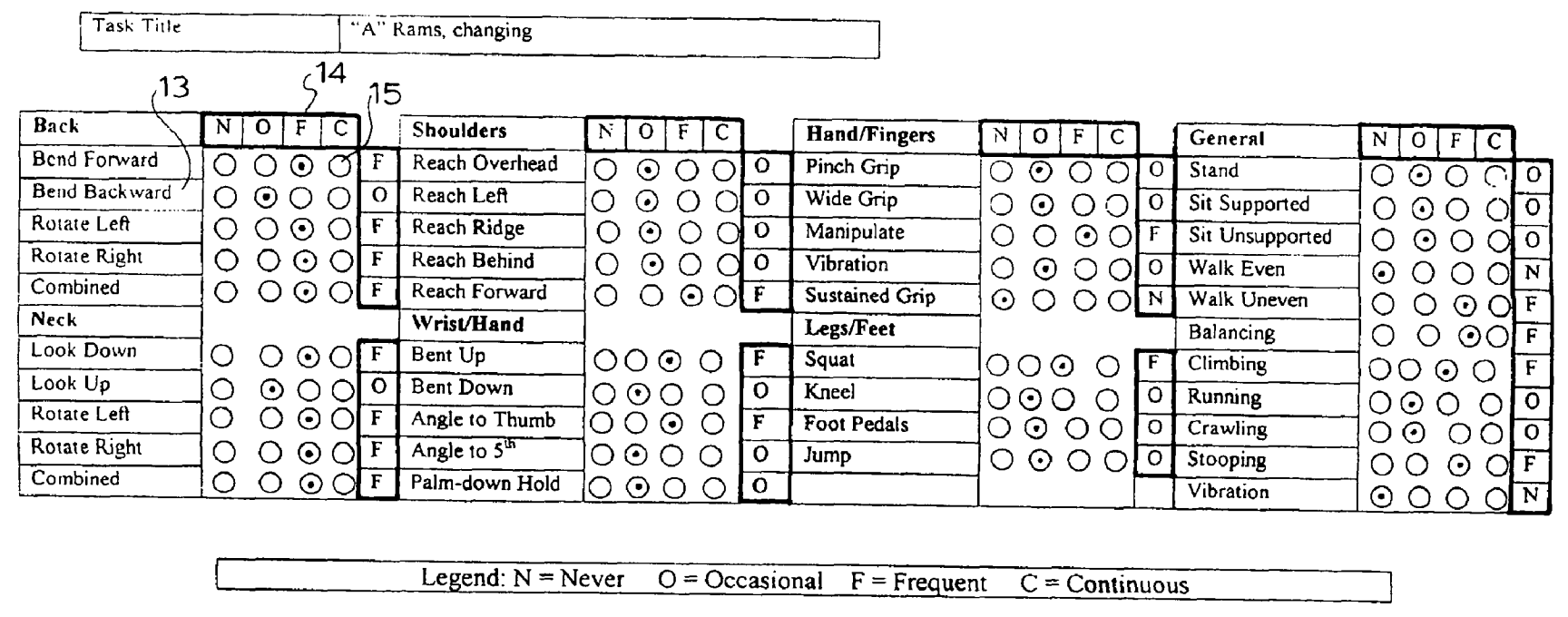

Details of a computer implementation of the invention will now be described with regard to FIGS. 2 to 9.

Initially in step 10 a computer is configured by entering details of each task or job into a task file in step 11 and storing each file in a task file data base 12. Thus in step 11 a physical task table is displayed through a GUI as shown in FIG. 4.

The GUI represents a number of working postures in a table format similar to that shown in FIG. 1 and as previously described.

For each working posture such as bending backwards represented by item 13, one of the frequency options 14 is completed by making an entry in the appropriate circular box 15.

In this example the physical task of changing "A" Rams requires occasional bending backward of the back. Therefore the box for "occasional" is completed and indicated in this example by a dot.

Each of the other physical activities are completed according to the physical requirements of the job of changing "A" Rams. When all of the physical task options have been completed another table is presented on the GUI as shown in FIG. 5. This table shows material handling ability requirements for the same task of changing "A" Rams. Thus each of the options of bench, shoulder, overhead, carry are completed by making an appropriate entry in the box for each different weight range 16 and each different frequency option 17.

The completed table then shows all the material handling requirements in which a person must engage in in order to perform the task of changing "A" Rams.

A summary page is also presented in the file which summarises the activities required for the job of changing "A" Rams. Additional comments and a task overview and task duration and frequency is also included along with the name of the assessor, date assessed, date modified and date of next review. The task file may also include information about the particular job in which the task is required such as in a long wall miner or long wall fitter and the frequency for performing the job and the division in which the job is required (e.g. underground coal). For each task a file is made and stored in the task file data base 12.

Figure 9:
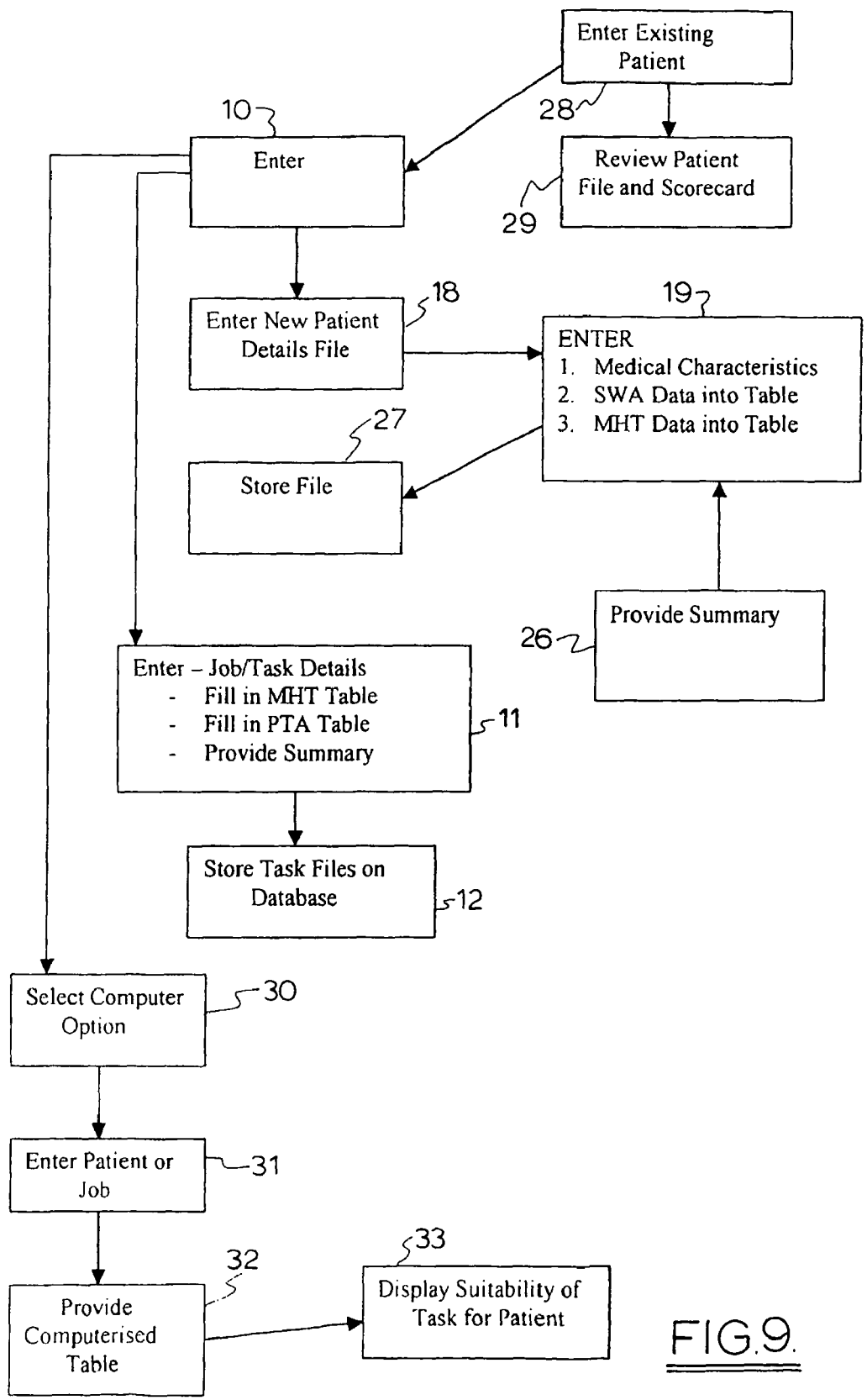
FIG. 9 shows a flow diagram of a system for controlling physical activities performed by a patient.

Files are then prepared for each rehabilitation patient by entering the new patient option 18 in FIG. 9. The GUI then presents a display which enables data to be entered about the patient in step 19.

Firstly details about the patient are entered and then as shown in FIG. 2 a table is presented to enable safe working ability data to be entered for the patient in relation to working postures. Thus for each working posture 20 the assessor must enter an appropriate frequency for performing the physical task which is appropriate having regard to the condition of the patient. A summary box 22 is also provided which provides a symbol representing the frequency with which each working posture can be performed.

When this table has been completed another table 23 is displayed which shows material handling options 24 and frequency options 25. According to the abilities of the patient the assessor allocates a value indicative of the ability of the patient to perform the particular material handling task. Thus as an example the ability to carry is shown to be permissible with a rating of 15 occasionally frequently with a rating value of 11 and continuously with a rating value of 8.5.

Once all details have been entered into the patient file a summary can also be added as shown in step 26 and the completed patient file is then stored in a data base in step 27.

If it is required to check the details of a patient the assessor or another person may enter the existing patient option in step 28 and review the patient file and a resultant score card in step 29, which score card combines the safe working ability and material handling tolerances acceptable to the patient.

Assuming data bases have been set up containing task files and patient files it is then possible to select a suitable job or task for any particular patient. Thus in step 30 if this is required a person such as an assessor may enter the computer program and on a menu page select the comparator option in step 30. The assessor is then presented with a request for entry of data relating to the worker and a particular job and division in step 31. When this information has been entered the assessor is able to select a job fit/comparison option which results in the computer program comparing data from the patient file and from the task file associated with that information entered by the assessor. This occurs in step 32. This results in a table being displayed showing different task activities 33 such as mechanical maintenance services or shovelling, the frequency 34 with which the task is required and a work postures count 35 and material handling count 36.

The working postures count 35 and material handling count 36 each have a suitable and unsuitable column 37, 38. For each task a number is shown in the suitable and unsuitable column representing the number of work postures suitable for the patient and the number of work postures which are unsuitable. Likewise a value is shown for the number of suitable material handling activities for the patient and a number of unsuitable material handling tasks for the patient.

Any box where 0 is entered in the unsuitable column is highlighted in a different colour such as green to boxes where there is a number other than 0 entered. Thus in FIG. 6 shuttle car driving is shown to have 39 suitable working postures and 0 unsuitable working postures. Likewise, there are 12 suitable material handling tasks and 0 unsuitable material handling tasks. This means that the patient is able to perform shuttle car driving without adversely affecting their condition.

Figure 7:
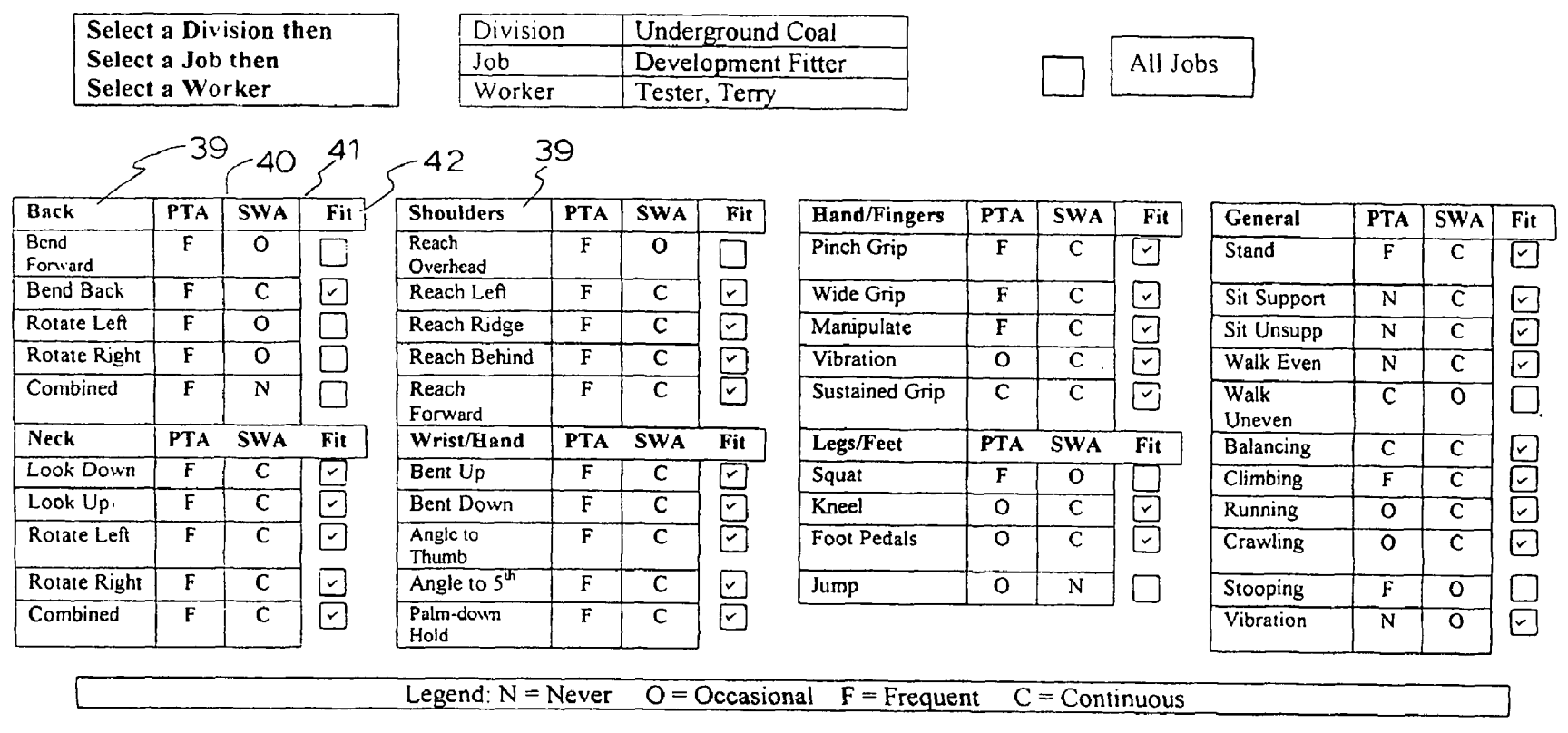

More detailed information about the capability of the patient for particular tasks is shown in table displays of FIGS. 7 and 8.

In FIG. 7 a working postures fit for the patient is shown in table form. Thus for each working posture 39 a box is provided in both a physical task ability column 40 and a safe working ability column 41. As long as the safe working ability is higher than the physical task requirement in column 40 the fit column 42 shows a tick. Thus for the physical posture of bending the persons back backward, the physical task requirement is that this be performed frequently and for the patient Terry Tester the safe working ability is for this task to be performed continuously. Therefore the patient is able to carry out this task and a tick is entered in the fit box. The same process is carried out for each of the other working postures and an assessor can immediately see which working postures are able to be performed by the patient.

In FIG. 8 material handling information is shown in table form with material handling options 43 being shown in rows and the physical task ability and safe working abilities shown in columns represented by items 44 and 45. In addition a fit column 46 is also provided. As each of the material handling tasks can be performed at different frequencies, the three columns 44, 45 and 46 are provided for each of the frequency options "occasional", "frequent", "continuous". In the example of the material handling task of carrying, the physical task requirement has a value of 35, whereas the safe working ability of the patient is 15, therefore no fit is entered in the fit box of column 46. For frequent carrying the physical task requirement has a value of 34 and a safe working ability is only 11. Therefore again there is no tick in the fit box.

Finally for continuous carrying the physical task requirement is only 3 and the safe working ability of a patient is 8.5. Therefore the patient is able to perform this task and a tick is entered in the fit box.

Thus referring back to FIG. 9 it is possible for an assessor to compare a patient's ability with any particular task requirement and in step 33 to display any material handling tasks where it is okay for the patient to perform that task.

From the above it should be apparent that in a working environment a worker who has suffered an ailment is able to be rehabilitated in a controlled fashion utilising the concepts of the invention.

It is to be understood that, if any prior art publication is referred to herein, such reference does not constitute an admission that the publication forms a part of the common general knowledge in the art, in Australia or in any other country.

The invention claimed is:

1. A method of assessing suitability of any of a number of persons for performing any of a number of task types which each require performance of a plurality of physical tasks utilising a computing system, including the steps of:

the computing system providing a task-type database having a plurality of task files which each relate to a task type which comprises a number of specific, repeatable physical tasks, and which each have data relating to physical task requirements required of a person performing that task type, and a plurality of frequency requirements which indicate a required frequency of performance for performing at least one physical task required in performance of said task type to which the task file relates;

the computing system providing a personal data file for each of a number of persons, each personal data file including data relating to allowable physical tasks which can be performed with an acceptable degree of safety by the person to whom the personal data file relates and to allowable frequency limits for the person when performing the at least one physical task;

the computing system providing a first interface to allow a user to select a personal data file, which relates to a person whose suitability it is desired to assess;

utilising the computing system to compare a selected personal data file, having a selected person's allowable physical tasks and allowable frequency limits data, with at least one task file having data relating to the physical task requirements and the frequency requirements of a corresponding task type; and from the comparison, generating by the computing system a first number representing a suitable number of work postures and a second number representing an unsuitable number of work postures for each task type for the selected person; and the computing system further providing a second interface concurrently displaying the first number and the second number for each task type for the selected person.

2. The method as claimed in claim 1 wherein the step of utilising the computing system to compare comprises a further step of performing a plurality of comparison procedures including comparing each physical task requirement with each allowable physical task.

3. The method as claimed in claim 2 wherein the comparison compares each allowable frequency limit data for each physical task, as set out in the selected personal data file with the frequency requirement data of each physical task required for the task type in the task file.

4. The method as claimed in claim 1 wherein each personal data file comprises a patient file having particulars about a patient.

5. The method as claimed in claim 4 including the step of providing a patient database having a plurality of patient files.

6. The method as claimed in claim 5 wherein each task file includes a plurality of required physical tasks and a plurality of frequency options which indicate the required frequency of performance for performing each required physical task, and each personal data file includes a plurality of allowable tasks and a plurality of frequency options which indicate an allowed frequency of performance of each allowable task, and at least some of the required tasks correspond exactly to at least some of the allowable tasks.

7. The method as claimed in claim 6 wherein each plurality of the frequency options includes options designated never, rarely, occasionally, frequently and continuously.

8. The method as claimed in claim 7 wherein a physical task analysis is displayed within a third interface in a table format with physical tasks arranged in rows and frequency options in columns.

9. The method as claimed in claim 8 wherein each physical task has the same possible frequency options.

10. The method as claimed in claim 9 wherein the physical tasks include tasks performed by different parts of a body.

11. The system as claimed in claim 9 wherein the physical tasks include different work postures.

12. The method as claimed in claim 9 wherein the physical tasks include different material handling options.

13. The method as claimed in claim 12 wherein each task file includes physical tasks and frequency options displayed with markings indicating frequency with which each physical task is required for the task type of that file.

14. The method as claimed in claim 13 wherein the different material handling options include different weights to be handled in different physical actions.

15. The method as claimed in claim 14 wherein the patient file includes a physical task analysis including a display of each allowable physical task versus frequency options for that task and an indication of any physical task which can be performed safely.

16. The method as claimed in claim 15 wherein the allowable physical tasks include allowable work posture and material handling tasks.

17. The method as claimed in claim 16 including the step of using a materials handling calculator for calculating a materials handling value for each material handling option performed at a particular frequency, the value being indicative of a required amount of physical activity for the material handling option.

18. The method as claimed in claim 2 wherein the comparison includes a comparison display having a list of tasks and a suitability indicator which indicates whether a patient is suitable for each task.

19. The method as claimed in claim 18 wherein the comparison display includes a work postures count value for each task type, the count value being indicative of usage of a pertinent work posture.

20. The method as claimed in claim 18 wherein the comparison display includes a materials handling count value for each task type which count value is indicative of a degree of usage of the material handling option.

21. A computer readable medium including computer program code, which when executed on a computing system, causes the computing system to assess suitability of any of a number of persons for any of a number of task types which each require performance of a plurality of physical tasks, the assessment comprising the steps of:

the computing system providing a task-type database having a plurality of task files which each relate to a task type which comprises a number of specific, repeatable physical tasks, and which each have data relating to physical task requirements required of a person performing that task type and a plurality of frequency requirements which indicate a frequency for performing at least one of the physical tasks required in performance of said task type;

the computing system providing a personal data file for a selected person including data relating to allowable physical tasks and allowable frequency limits for the selected person when performing each task type;

the computing system arranged to operate a comparison operation for comparing a file having a selected person's allowable physical tasks and allowable frequency limits data with a task file having data relating to the physical task requirements and the frequency requirements of each task type;

the computing system arranged to generate, from the comparison operation, a first number representing a suitable number of work postures and a second number representing an unsuitable number of work postures for each task type for the selected person; and the computing system arranged to provide an interface concurrently displaying the first number and the second number for each task type for the selected person.

22. The method as claimed in claim 1, wherein at least one task type is a vocational job or an action which is part of the vocational job and the method includes assessing the suitability of the person to whom the selected personal data file relates for performance of the job or part thereof.

23. The method as claimed in claim 1, wherein:

task files of the task-type database are created with at least some of the data relating to a corresponding task type's physical task requirements, and at least some of the data relating to the corresponding task type's frequency requirements, arranged in a predetermined format; and personal data files are created with at least some of the data relating to a corresponding person's allowable physical tasks and at least some of the data relating to the corresponding person's allowable frequency limits data, arranged in a predetermined format;

wherein a format of at least some of the physical task requirements of the task files is the same as a format of data relating to corresponding allowable physical tasks of the personal files, in order to facilitate the comparison.

24. The method as claimed in claim 1, further comprising the steps of:

creating at least some of the task files of the task-type database by entry of data relating to said physical task requirements and of data relating to said frequency requirements, of the task type for a corresponding task file, into at least one task-type data entry form which provides predetermined fields for entry of said task type data in a predetermined format; and creating at least some of the personal data files by entry of data relating to a corresponding person's allowable physical tasks and allowable frequency limits data, into at least one personal data entry form which provides predetermined fields for entry of said personal data in a predetermined format;

wherein the predetermined fields of the task type data entry form for at least some of the physical task requirements of the task files correspond directly to the predetermined fields of the personal data entry form relating to allowable physical tasks of the personal files.

25. The method as claimed in claim 24, wherein the predetermined fields of the task type data entry form for the frequency requirements of at least some of the physical task requirements of the task files correspond directly to the predetermined fields of the personal data entry form relating to allowable frequency limits of corresponding allowable physical tasks of the personal files, in order to facilitate the comparison.

* * * * *